United States Patent [19]

Wiland

[11] 4,270,902
[45] Jun. 2, 1981

[54] METHOD AND APPARATUS FOR CARVING AND CONTOURING DENTAL RESTORATIONS

[76] Inventor: Lawrence Wiland, 144-15 41st Ave., Flushing, N.Y. 11355

[21] Appl. No.: 970,362

[22] Filed: Dec. 18, 1978

[51] Int. Cl.³ .............................................. A61C 3/02
[52] U.S. Cl. .................................... 433/144; 433/143; 433/70
[58] Field of Search ...................... 32/46, 42, 40 R, 15, 32/41, 50, 51; 433/144, 143, 70, 196, 197, 213, 223

[56] References Cited

U.S. PATENT DOCUMENTS

| | | | |
|---|---|---|---|
| 1,369,582 | 2/1921 | Wagner | 32/46 |
| 1,455,374 | 5/1923 | Ziesel | 32/46 |
| 1,497,749 | 6/1924 | Diack | 32/46 |
| 1,691,786 | 11/1928 | Roth | 32/50 |
| 1,857,396 | 5/1932 | Peck | 32/46 |
| 1,875,680 | 9/1932 | Van Horn | 32/46 |
| 2,752,681 | 7/1956 | Jankelson | 32/19 |
| 4,183,139 | 1/1980 | Tanaka | 433/70 |

OTHER PUBLICATIONS

Parkell Co., New York, Catalog, 1956, p. 15.
Silverman's Catalog, 1976, p. 23.

Primary Examiner—Gene Mancene
Assistant Examiner—John J. Wilson
Attorney, Agent, or Firm—Harvey B. Jacobson

[57] ABSTRACT

The finishing of dental restorations is disclosed with use of dental instruments of the present invention including instruments having concave surfaces shaped to conform to external convex tooth anatomy. External carving and contouring is accomplished by first carving the distal, mesial, lingual and facial convex surfaces using an interproximal carving instrument of the present invention, followed by carving of adjacent marginal ridges and contact areas, and embrasures with an intermarginal carver. Internal carving and contouring is accomplished by first making the areas of fossae and basic occlusal grooves with the ball end of the intermarginal carver, followed by carving and contouring tooth cusps and cuspal inclines, and then supplemental or developmental grooves with an occlusal-incisal carver.

4 Claims, 24 Drawing Figures

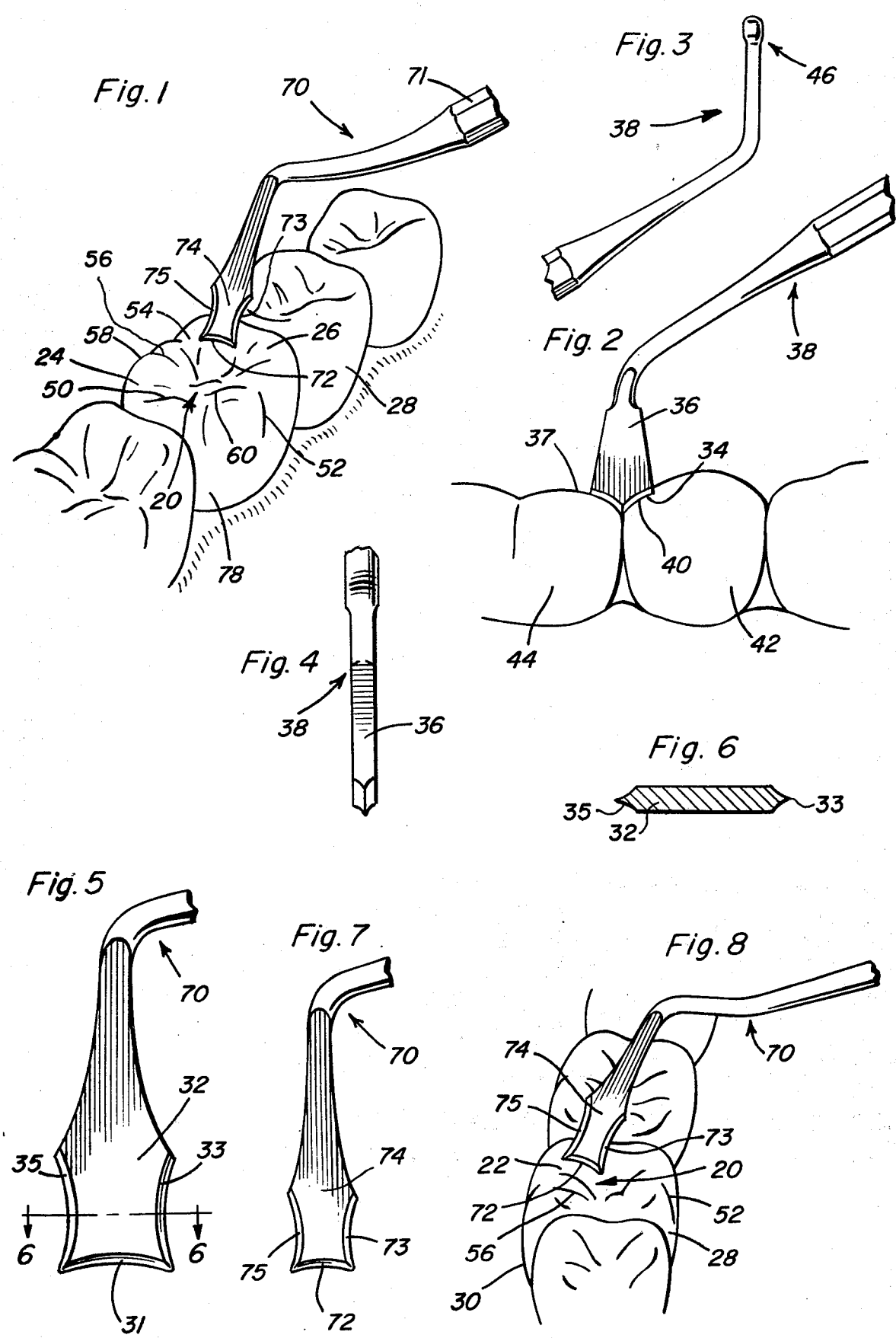

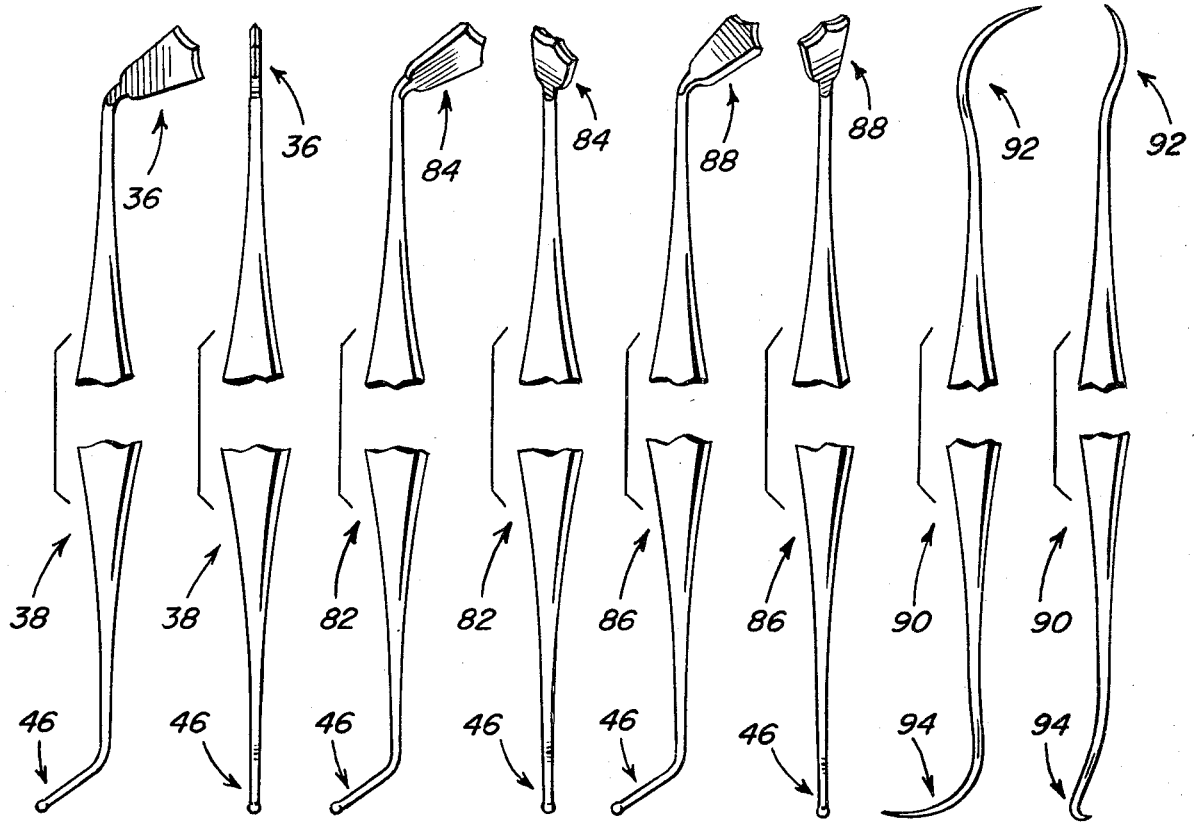
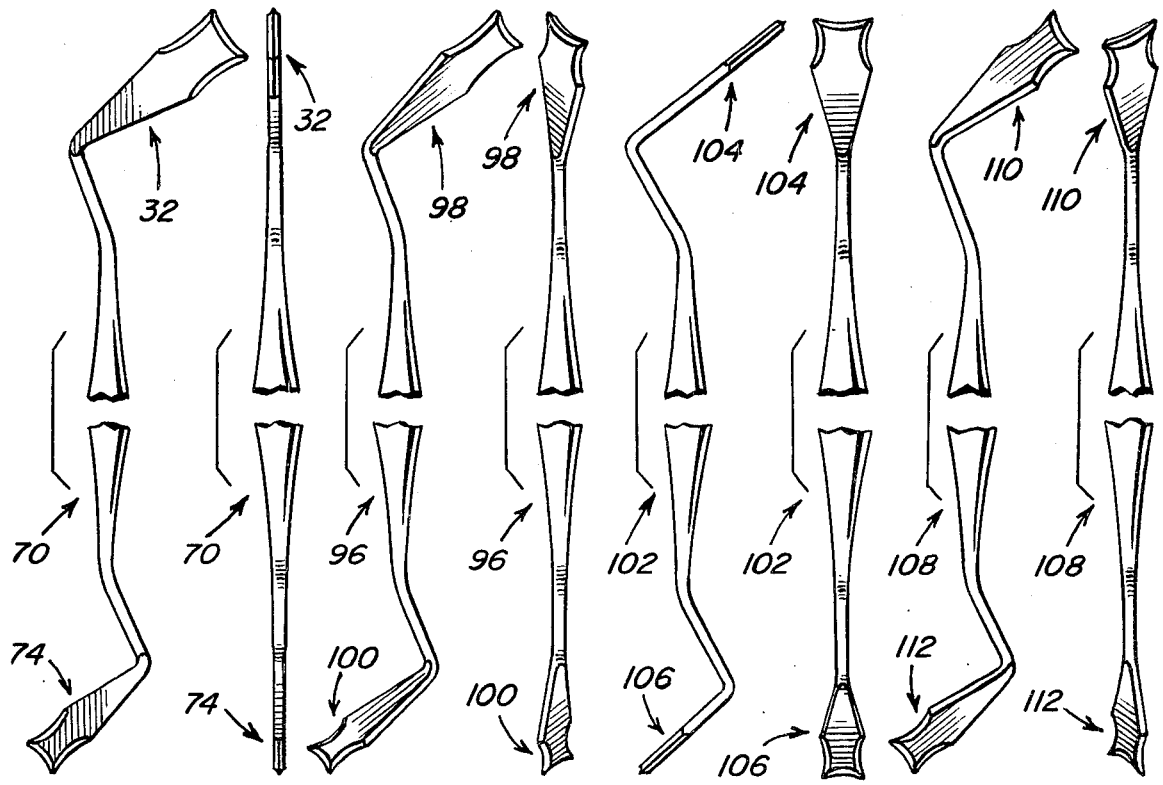

METHOD AND APPARATUS FOR CARVING AND CONTOURING DENTAL RESTORATIONS

BACKGROUND OF THE INVENTION

1. Field of the Invention

The invention relates to finishing of dental restorations. More particularly, the invention discloses a method for external and internal carving and contouring of convex surfaces of tooth anatomy, as well as ridges, contact areas, embrasures, fossae and grooves. The invention also includes instruments for carrying out the method of finishing dental restorations, including an interproximal carver, an occlusal-incisal carver, and an intermarginal carver, the latter two of which have concave surfaces constructed to match the convex surfaces of external tooth anatomy. The position of the plane of the concave carving edges varies in different embodiments of the invention, to allow the operator to select instruments appropriate to the particular quadrant.

2. Description of the Prior Art

Many general background references pertinent to the field of dentistry embraced by the present invention are available from state dental associations and publishers of scientific material.

A dental tool is disclosed in U.S. Pat. No. 1,497,749, issued June 17, 1924, to Diack, where a method for working the occlusal contour of a single tooth is disclosed, along with instruments for accomplishing burnishing of dental surfaces by a V-edge. U.S. Pat. No. 1,875,680, issued Sept. 6, 1932, to Van Horn, shows a carving instrument for shaping a wax model of a tooth, specifically adapted for pushing and pulling in following the tooth form.

U.S. Pat. No. 1,953,584, issued Apr. 3, 1934, to Bronner, mentions that the dental tool described therein has an operative surface or cutting edge of suitable contour.

Other patents describing dental instruments for various purposes are the following:

U.S. Pat. Nos.
- 550,508—Nov. 26, 1895—How
- 888,071—May 19, 1908—Dodez
- 1,109,924—Sept. 8, 1914—Hoffman et al.
- 1,382,401—June 21, 1921—Zurbrigg
- 3,023,501—Mar. 6, 1962—Schmitt.

SUMMARY OF THE INVENTION

Prior dental tools for contouring or carving of dental restorations have typically been designed in a convex shape, pointed shape, or other shapes not conforming to the convex surfaces characterizing all external tooth anatomy. Moreover, prior dental implements have not been specifically adapted for intermarginal carving of two adjacent teeth. Furthermore, a method for carving and finishing dental restorations has not been described making use of the advantages of the instruments of the present invention.

Accordingly, it is an object of the present invention to provide a dental carving instrument having concave surface for conformingly carving or shaping convex outer surfaces of dental restorations.

Another object of the invention is to provide a dental instrument for intermarginal carving of two adjacent teeth.

Yet another object is to provide a dental instrument for occlusal-incisal carving of a single tooth.

Still another object of the invention is to provide a method for external carving and contouring of dental restorations, as well as a method for internal carving and contouring of dental restorations.

A further object of the invention is to provide a method for dental carving relying upon guiding of a dental carving instrument by the unprepared tooth structure.

Yet a further object of the invention is to provide a method for use of the interproximal, intermarginal and occlusal-incisal dental instruments of the present invention.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a fragmentary perspective view of one end of a double-ended occlusal-incisal dental carver in association with a molar dental restoration.

FIG. 2 is a fragmentary side elevational view of an intermarginal dental carving instrument in use for carving a dental restoration where the instrument is inserted in the margin between two adjacent teeth.

FIG. 3 is a fragmentary side elevational view of the ball end of an intermarginal dental carving instrument, such as is associated with the instrument of FIG. 2.

FIG. 4 is a fragmentary edge elevational view of the intermarginal instrument of FIG. 2 viewed from the left of FIG. 2 in the rightward direction.

FIG. 5 is a fragmentary side elevational view of the opposite end of the occlusal-incisal instrument of FIG. 1.

FIG. 6 is a transverse sectional view of the instrument of FIG. 5, taken substantially upon a plane passing along section line 6—6 on FIG. 5.

FIG. 7 is a side elevational view of the end of the instrument shown in FIG. 1.

FIG. 8 is a perspective view of the instrument of FIG. 1 in association with a molar dental restoration, showing the instrument guided in use by the unprepared tooth structure.

FIGS. 9-24 are elevational views of a set of eight dental carving instruments, where the odd numbered drawings show side elevational views and the next higher even numbered drawing shows the same instrument rotated axially through 90° in an edge elevational view. Accordingly, the three pairs of drawings comprising FIGS. 9-14 show three intermarginal instruments of differing head orientation, each instrument having an opposite ball end. FIGS. 15-16 show an interproximal carver; and FIGS. 17-24 show four occlusal-incisal instruments having varying head orientations.

DESCRIPTION OF THE PREFERRED EMBODIMENT

External tooth anatomy consists of elevations or projections and depressions. The elevations consist of cusp tips or peaks, cuspal inclines or slopes, marginal ridges and marginal inclines, while the depressions consist of grooves or sulci, pits, and fossae, which occur where three grooves intersect. A pit is a small depression with a fossa, and grooves or sulci occur at the base intersection line of two adjacent inclined surfaces. Teeth consist of a series of multiple convex surfaces, as can be seen in FIG. 1. Each and every tooth is distinctly different in its surface convex anatomy. It has been found that a convex surface of a dental restoration can be best carved, contoured and finished by a substantially matching concave edge of a dental instrument, such as concave distal edge 72 and concave side edges 73 and 75 on head 74 of instrument 70 shown in FIG. 1. The finishing of dental restorations is accomplished more adequately when carving, rotary and finishing instruments are designed and used for maximum surface contact.

The direction of carving should be parallel to the cavosurface margin in its total outline. As is illustrated in FIG. 1, head 74 of instrument 70 should be directed at right angles to the cavosurface margin along the groove and fossa pattern of tooth 78 and restoration 20 within tooth 78. The ideal technique for carving or finishing involves use of unrestored surfaces for guiding instrument 70 by contact with an instrument surface. For instance, in FIG. 8, surface 22 is used in guiding carver 70 in carving restoration 20. Only one unprepared guide surface is usually possible in this technique. Each and every surface forming part of restoration 20 must be carved. Three surfaces must be carved within the area of a fossa, and two surfaces must be carved within the area of a groove and cuspal incline. For maximum visibility of the tooth during carving and finishing, work on restoration 20 should proceed generally from distal surface 24 toward mesial surface 26, and from lingual surface 28 toward facial surface 30. The margins should reflect the correct convex contour of the tooth, and choice of the carving instrument should be selected to most closely match the curvature of the concave edge of the instrument to the curvature of the convex surface to be carved. For instance, the greater degree of curvature of edge 72 of head 74 of instrument 70, as shown in FIG. 7, most closely matches a tooth surface having a sharply curving convexity, while the lesser degree of curvature of the concave edge 31 of wide instrument head 32, as shown in FIG. 5, more closely matches a convex tooth surface of lesser curvature. As illustrated in FIGS. 5 and 7, the longitudinal direction of side edges 33 and 35 or 73 and 75 is substantially perpendicular to the longitudinal direction of distal edge 31 or 72. Other concave edges 33 and 35 can also be used for carving of the tooth surfaces and are approximately the same length as edge 31. Adjacent proximal margins should be in harmony with respect to their four embrasure spaces. The proximal contact area should be placed about one millimeter gingival to the occlusal surface.

External carving and contouring is accomplished by carving the distal, mesial, lingual and facial surfaces using the concave edge 72 of head 74 of occlusal-incisal instrument 70. If restoration 20 extends to the margin between adjacent teeth, adjacent marginal ridges are placed in contact with the concave end 36 of intermarginal carver 38, as shown in FIG. 2, using the unrestored ridge as a guiding surface. For example, if ridge 34 is to be restored, concave edge 40 of intermarginal carver 38 is used for carving the convex surface of tooth 42 in substantially its original form, while unrestored ridge 37 of tooth 44 is used as the guiding surface. Intermarginal carver 38 is constructed so that by virtue of the design of carver 38 its contact area is about one millimeter gingival to the occlusal surface. Included in the external carving and contouring operations should also be development of the four embrasures (occlusal, facial, lingual and gingival).

Internal carving and contouring proceeds first by marking of the fossae, including the distal, central and mesial, falling within the region of the restoration. This marking is accomplished with ball end 46 of intermarginal carver 38, or, alternatively, with a separate instrument having a ball end. The basic occlusal grooves are then marked in the region of the restoration with the same ball end, including the buccal, lingual, distal and mesial grooves, such as distal groove 50, lingual groove 52, mesial groove 54 and buccal groove 56. Cusps and cuspal inclines are then carved by one of the concave edges 72, 73 or 75 of occlusal-incisal carver instrument 70, such as cusp 58. Next, carving and contouring of supplemental or developmental grooves, such as supplemental groove 60, is accomplished with the concave edge 72 of head 74 of instrument 70.

Proper interfitting of the restored tooth is evaluated through hinge and translatory jaw movements both under and not under the dentist's control to determine overfilling or overcontouring of the restored surfaces. Both centric occlusion and eccentric occlusion are considered. Finally, all margins are checked to insure complete coverage, carving and contouring, as well as a smooth blending of restoration to tooth and tooth to restoration. Contact areas must be in the correct facial, lingual and occlusal gingival proportions, and positive contact with extra-fine dental floss should result.

Additional structural details of intermarginal carving instrument 38 are shown in the edge seen in FIG. 4, and the sectional view of the occlusal-incisal instrument 70 shows in FIG. 6 details of construction of head 74. FIGS. 5 and 7 point out instruments having differing degrees of concavity in a pair of occlusal-incisal dental carving instruments.

While intermarginal carver instrument 38 has been illustrated in the form of a double-ended carver having a concave end and a ball end 46 as seen in FIG. 3, it is within the scope of the present invention to provide other instruments having the ball end 46. Preferably, however, the ball end is associated with the intermarginal carver for reasons of convenience in operation according to the method of the invention. While the present invention is concerned primarily with instruments having concave edges suitable for carving substantially conforming convex tooth restoration surfaces, the ball end 46 not per se forming a distinctly independent part of the present invention, the combination of a concave edged instrument end with a ball end is contemplated within the scope of the present invention, as well as a method utilizing such an instrument.

In FIG. 9 the relative orientation of each end of intermarginal carver 38 is pointed out, including concave end 36 and ball end 46. FIG. 10 shows the same features from a different direction of view, where the instrument of FIG. 9 has been rotated through 90°. Similarly, FIGS. 11 and 12 show features of instrument 82, distinguished from instrument 38 by the orientation of concave end 84, and FIGS. 13 and 14 show features of instrument 86 in a somewhat different orientation of concave end 88. p FIGS. 15 and 16 show interproximal instrument 90, bringing out the twisted nature of the pointed heads 92 and 94.

FIGS. 17 and 18 show occlusal-incisal instrument 70, including wide instrument head 32 and narrower instrument head 74 on the opposite end of instrument 70. Heads 32 and 74 are seen to lie in a plane passing through the axis of instrument handle 71. FIGS. 19 and 20 show occlusal-incisal instrument 96, with details of construction and orientation of wide head 98 and narrower head 100. Similarly, FIGS. 21 and 22 show occlusal-incisal instrument 102, with wide head 104 and narrower head 106; and FIGS. 23 and 24 show occlusal-incisal instrument 108 with wide head 110 and narrower head 112.

Various head orientations are provided in order to permit a skilled operator to choose the instrument appropriate for a particular quadrant of the mouth of the patient on whom dental restoration work is performed. The Table discloses recommended instruments by mouth quadrant for use by a right-handed operator.

TABLE

| Recommended Instruments for Right-Hand Operators | |
|---|---|
| Mouth Quadrant | Instrument Number |
| Upper right | 70, 102, 86 and 90 |
| Upper left | 102, 108, 82 and 90 |
| Lower left | 70, 96, 86 and 90 |
| Lower right | 70, 102, 38, and 90. |

Instrument numbers in the Table correspond to the reference numerals applied to the instruments of FIGS. 9-24. Instruments, of course, can be used by left-handed operators by interchange of instruments 82 and 86, by interchange of instruments 96 and 102, and by an appropriate modification of interproximal instrument 90.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An occlusal-incisal dental carving instrument comprising a handle and a flattened head carried by said handle, the head terminating in a concave distal edge and having a pair of concave side edges, the longitudinal direction of said side edges being substantially perpendicular to the longitudinal direction of said distal edge, the length of said distal and side edges being substantially the same, said distal and side edges utilized for carving of a dental restoration on the occlusal surface of a tooth.

2. A method of external carving, contouring, and finishing a dental restoration of a human tooth, the method comprising the following steps:
   (a) carving the distal, mesial, lingual and facial surfaces of the dental restoration using an interproximal carver comprising a handle and arcuate pointed head carried by said handle; and wherein said tooth has an occlusal surface defined by proximal marginal ridges; and
   (b) carving the proximal marginal ridges of said tooth with an intermarginal carver about one millimeter gingival to said occlusal surface, said intermarginal carver comprising a handle and flattened head carried by said handle, the head having a pair of concave edges conforming substantially to the shape of the original tooth surface.

3. The method of claim 2 wherein said interproximal carver is guided in its carving and contouring movement by an unrestored ridge of said tooth.

4. The method of claim 2 wherein the proximal ridges have differing degrees of curvature and a plurality of intermarginal carvers having concave edges of differing degrees of curvature are employed to carve said ridges.

* * * * *